United States Patent [19]

Velasquez

[11] Patent Number: 4,736,397
[45] Date of Patent: Apr. 5, 1988

[54] RADIATION IMAGE INSPECTION APPARATUS

[75] Inventor: Juan F. Velasquez, Saline, Mich.

[73] Assignee: Applied Intellegent Systems, Inc., Ann Arbor, Mich.

[21] Appl. No.: 809,247

[22] Filed: Dec. 16, 1985

[51] Int. Cl.$^4$ .................. H05G 1/64; G01N 23/04
[52] U.S. Cl. ........................... 378/99; 378/58; 378/114; 378/116; 358/111
[58] Field of Search ........... 378/99, 98, 106, 116, 378/57, 58, 62, 114; 250/483.1; 358/111

[56] References Cited
U.S. PATENT DOCUMENTS

| | | | |
|---|---|---|---|
| 3,919,467 | 11/1975 | Peugeot | 378/99 |
| 4,041,319 | 8/1977 | Fukuzawa et al. | 250/483.1 |
| 4,139,771 | 2/1979 | Dennhoven et al. | 378/99 |
| 4,193,089 | 3/1980 | Brougham et al. | 358/111 |
| 4,346,406 | 8/1982 | Kato et al. | 358/110 |
| 4,473,843 | 9/1984 | Bishop et al. | 358/111 |
| 4,562,464 | 12/1985 | Kurihara | 378/99 |
| 4,612,572 | 9/1986 | Komatsu et al. | 358/111 |

Primary Examiner—Carolyn E. Fields
Assistant Examiner—Joseph A. Hynds
Attorney, Agent, or Firm—Basile, Hanlon

[57] ABSTRACT

A radiation image inspection apparatus for inspecting articles. The inspection apparatus includes a radiation source which generates and directs radiation, preferably x-rays, toward and around the article. The radiation penetrates and passes around the article and strikes a screen having a coating formed of a rare earth element. The coating exhibits fluorescence when struck by incident radiation and becomes illuminated, generating a first light image of the article. The first light image passes through a plurality of lenses which maintain the intensity of the light image before striking a camera having a front camera screen. The camera by means of an internal sweep beam scans the camera screen and generates an electrical output signal corresponding to the image on the camera screen. A controller controls the operation of the camera and radiation source in either of two modes. In the first mode of operation the radiation source is energized to continually generate radiation and the camera output is blanked for a pre-determined amount of time after the inspection sequence begins to enable radiation energy to build up on the screen thereby maximizing the intensity of the visible light image generated on the screen. At the end of the pre-determined time interval, the camera is activated to generate a signal corresponding to the image on the camera screen. In the second mode of energization, the radiation source and the camera are pulsed for a short time period, with the radiation source being energized at a high intensity level.

7 Claims, 1 Drawing Sheet

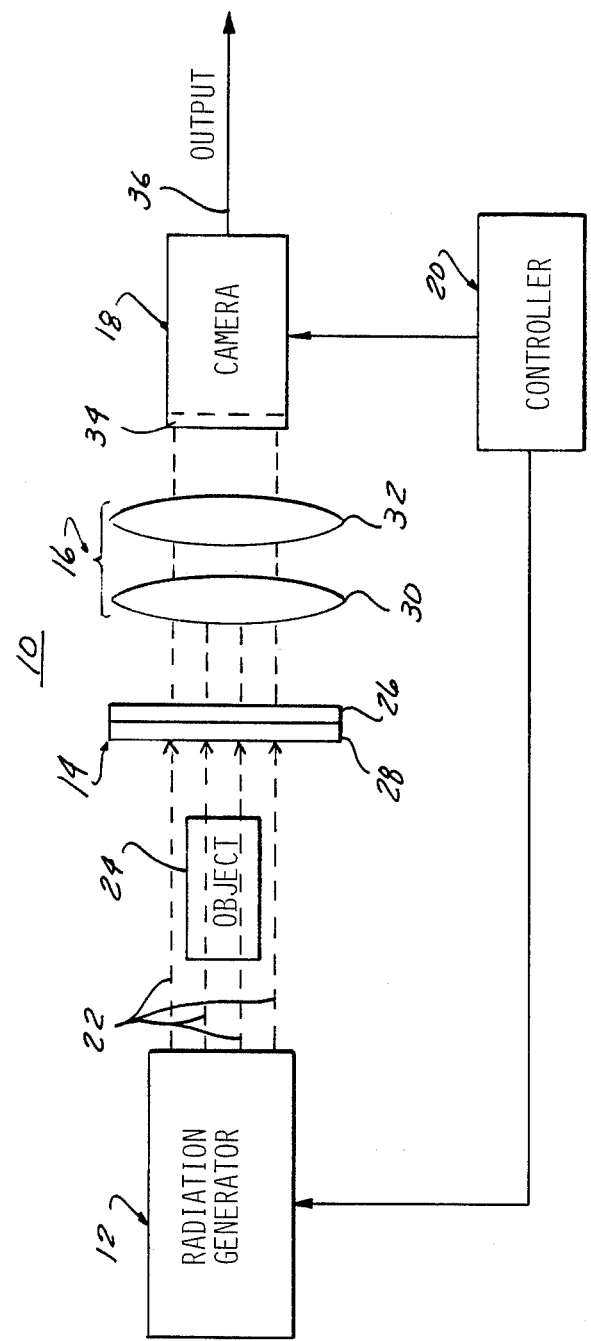

RADIATION IMAGE INSPECTION APPARATUS

BACKGROUND OF THE INVENTION

1. Field of the Invention

This invention relates, in general, to article inspection apparatus and, more specifically, to article inspection apparatus which converts the radiation pattern of an article or object into a visible light image.

2. Description of the Prior Art

Radiation, particularly x-rays, is used in many different fields to inspect articles, such as manufactured parts, packages, etc. for defects, surface cracks, internal foreign objects, etc., as well as in medical diagnostic procedures for examining patients. In such inspection or diagnostic apparatus, radiation from a suitable source is directed at and penetrates the article or patient. The radiation, some of which is absorbed by the article, is then received by the screen of a conventional camera which produces a light image corresponding to the radiation pattern of the object. Such exemplary inspection systems are shown in U.S. Pat. Nos. 4,193,089 and 4,473,843.

It is also known to direct the radiation through an object onto a stimulatable phosphor screen which records the radiation image and which can be read out by use of stimulating rays directed onto the screen.

In all such cases, it has been found that light images produced on the camera screen or on the stimulatable phosphor screen are relatively low in intensity thereby making it difficult to obtain a clear and easily viewable image of the object. Such clearness is essential in inspecting the surface of manufactured parts for minute defects, such as surface cracks, which can only be a few millionths of an inch in width or length.

To overcome these problems, it is conventional to employ an x-ray detector and light intensifier between the object and the camera as shown in U.S. Pat. No. 4,473,843. Such an image intensifier includes a series of lenses and electronic circuits which amplify the image impinging upon the screen at one end of the intensifier and display the amplified image at a screen at a second end which can be detected by the camera. However, while such image intensifiers are effective at improving the x-ray produced image, such image intensifiers are expensive and relatively long in length thereby increasing the overall size of inspection apparatus and adding to its total cost. Such intensifiers are also subject to scintillation noise which causes distortion of the viewed image.

Thus, it would be desirable to provide a radiation image inspection apparatus which overcomes the problems of previously devised radiation inspection apparatus. It would also be desirable to provide a radiation image inspection apparatus which eliminates the need for a conventional image intensifier. Finally, it would be desirable to provide a radiation image inspection apparatus which is small in size, has a relatively low manufacturing cost and is capable of producing clear images with a resolution of a few millionths of an inch.

SUMMARY OF THE INVENTION

The present invention is a radiation image inspection apparatus which generates a visible light image of the radiation pattern of an article.

The radiation image inspection apparatus includes a radiation source which generates and directs radiation toward the article. The radiation penetrates the article and a portion is absorbed depending upon the density and configuration of the article. A screen is mounted on the opposite side of the article from the radiation source such that the radiation passing through and around the article impinges upon the screen. Preferably, the screen is coated with a material which exhibits fluorescence properties. In a preferred embodiment, the coating is formed of a rare earth element, such as scandieum, yttrium or the lanthanides series of elements having atomic numbers from 57-71, as well as mixtures and alloys thereof. Any of these materials exhibits fluorescence when struck with radiation thereby illuminating portions of the screen depending upon the amount of radiation incident thereon. The illuminated portions of the screen correspond to a visible image of the article. The visible light image then passes through a plurality of lenses which maintain the intensity of the image before striking the front screen of a camera. The camera means generates electrical output signal corresponding to the first light image.

A control means or controller is connected to the camera and the radiation source of controlling the operation of both the camera and the radiation source in one of two modes of operation. In a first mode of operation, the controller maintains the radiation source in a constantly energized state such that the source continually directs its radiation onto the object. However, in order to maximize the intensity of the light striking the camera screen so as to produce images with high clarity, the controller holds the output of the camera in an off state for a pre-determined amount of time, such as one second, to enable the radiation energy to build up for the pre-determined time on the fluorescent screen. At the end of the blanking or off period, the controller activates the camera output.

In a second mode of operation, the controller energizes the radiation source in a strobe or pulse mode at a extremely high radiation intensity. The camera is also energized for the pulse time period in order to receive the image generated on the fluorescent screen.

The radiation image inspection apparatus of the present invention overcomes many of the problems encountered with previously devised inspection apparatus insofar as providing a visible light image having the requisite high resolution and clarity required to detect surface cracks, internal foreign objects, etc. of only a few millionths of an inch in length or width in or on the article. The radiation image inspection apparatus of the present invention makes unique use of a rare earth element coated screen and camera control circuit which eliminate the need for a conventional, elongated image intensifier.

Finally, the radiation image inspection apparatus of the present invention may be employed in either of two modes of operation thereby enabling it to be used to inspect stationary or continually moving objects. This increases the range of applications of the present inspection apparatus and enables it to be converted between different applications without extensive modifications.

BRIEF DESCRIPTION OF THE DRAWING

The various features, advantages and other uses of the present invention will become more apparent by referring to the following detailed description and drawing which depicts a schematic and block diagram of the radiation image inspection apparatus of the present invention.

DESCRIPTION OF THE PREFERRED EMBODIMENTS

There is depicted in the drawing a radiation image inspection apparatus 10 which is useful in inspecting articles, such as manufactured parts, packages, etc., for defects, such as surface cracks, as well as foreign objects imbedded within the object. In general, the inspection apparatus 10 includes a radiation source 12, a screen 14, intensifying lenses 16, a camera means 18 and a control means or controller 20.

The means for generating radiation 12 may be any conventional type of radiation generator. Preferably, however, the radiation generator 12 is capable of generating x-rays 22 which are directed toward an object 24 which is to be inspected. The x-rays 22 penetrate and pass around the surface edges of the object 24 and are partially absorbed by the object or are scattered thereby enabling the detection of foreign objects within the object 24 as well as the exact details of the surface edge configuration of the object 24.

It should be noted that the radiation source 12 and the object 24 shown in the drawing are depicted as being oriented along a common horizontal axis or plane. It will be understood, however, that the radiation source 12 may be positioned below the object 24 and the remaining elements of the inspection apparatus 10, such as the screen 14 and lenses 16, may be positioned above the object 24 along a common vertical axis with the radiation generating means 12.

As noted above, a screen 14 is provided for receiving the x-rays 22 generated by the radiation generator means 12 after such radiation or x-rays have passed through and around the object 24. The screen 14 functions to generate a visible first light image of the radiation pattern created by radiation passing through and around the object 24. It is preferred that the screen 14 exhibit fluorescent properties such that portions of the screen will become illuminated depending upon the amount of radiation incident thereon to produce a visible image.

The screen 14 is constructed of a substrate or base 26 on which a coating 28 of the fluorescent material is diposed. Preferably, the coating 28 is formed of a rare earth element, such as scandium, yttrium or one of the lanthanides series of rare earth elements having atomic numbers ranging between 57–71. These rare earth elements exhibit the desired fluorescent properties when struck with incident radiation, such as x-rays. Such elements also exhibit a fast response time to such incident radiation in reaching the illuminated state, as well as returning to a darkened or off-state after such radiation has been discontinued.

The light image generated on the base 26 as well as the radiation 22 passing through the screen 14 then is directed through a lens assembly 16. In a preferred embodiment, the lens assembly 16 is constructed with 3 to 6 lens elements, such as lens elements 30 and 32, which are arranged along a common axis.

The lens assembly 16 functions to maintain the light image generated on the screen 14 at a high intensity. Furthermore, it is preferred that the lens assembly 16 be constructed to block the radiation or x-rays 22 from striking the front lens of the camera 18. As such, the lenses, such as lenses 30 and 32, are preferably formed of heavily leaded glass which allow the light image to pass therethrough but blocks the radiation or x-rays 22.

After passing through the lens assembly 16, the visible light image impinges upon the front screen 34 of a conventional camera 18. Preferably the camera is of the vidicon type, although other types of cameras may also be employed in the radiation image and inspection apparatus 10 of the present invention. As is conventional, the camera 18 includes an internal sweep beam which scans the screen 34 in a plurality of horizontal, vertically spaced scan lines a number of times each second. A voltage is generated as the beam moves along the scan line depending upon the amount of light incident on one particular portion of the screen 34 which is converted to an electrical analog output signal 36. The output signal 36 may be used by subsequent devices, not shown, to reconstruct and display the visible image generated by the inspection apparatus.

Finally, the inspection apparatus 10 of the present invention includes a control means or the controller 20 which is connected to and controls the operation of both the camera 18 and the radiation generator 12. The control means or controller 20 may be a conventional computer having an internal software program which controls the operation of the camera 18 and the radiation generator 12. Alternately, a hard wired logic circuit may be employed for higher speed in controlling the operation of the camera 18 and radiation generator 12.

The controller 20 controls the operation of the camera 18 and radiation generator 12 in either of two selected modes of operation. In a first mode of operation, which is advantageous for use in inspecting objects 24 which are stationarily positioned in front of the radiation generator 12, the controller 20 maintains the radiation generator 12 in a constantly energized state so as to produce a constant stream of radiation 22. The controller 20, when the inspecting sequence has started, maintains the output 36 of the camera 18 in an off or blanked position for a pre-determined amount of time, such as one second, during which the radiation builds up additional charge on the screen 14 thereby intensifying the visible light image generated on the screen 14. At the end of the pre-determined blanking or off period, the controller 20 activates the camera 18 to scan the camera screen 34 and to generate an output signal 36. The amount of blanking time is selected depending upon several factors such as the exposure level desired, the density of the object 24, as well as the intensity of the radiation 22 produced by the radiation generator 12.

In a second mode of operation, the inspection apparatus 10 is suited for use with constantly moving objects, such as objects moving along a conveyor between the radiation generator 12 and the screen 14. In this mode of operation, the controller 20 energizes the radiation generator 12 in short pulses. Furthermore, the controller 20 activates the radiation generator 12 to produce an extremely high level radiation intensity, approximately one hundred times higher than the radiation intensity utilized in the first mode of operation with stationary positioned objects 24. At the same time, the controller 20 activates the camera 18 for the same short pulse period to scan the image on the camera screen 34 and to produce the output signal 36.

Thus, the controller 20 controls the operation of the camera 18 and the radiation generator 12 by controlling the amount of on or off time of both the camera 18 and the radiation generator 12 when activated as well as controlling the output from the camera 18.

In summary, there has been disclosed a unique radiation image inspection apparatus which produces images of high clarity and resolution thereby enabling its use to detect cracks and defects in the surface of various articles, such as manufactured parts, having a size of only a few millionths of an inch in length or width. The radiation image inspection apparatus of the present invention also eliminates the need for the elongated, expensive image intensifiers employed in previously devised radiation inspection apparatus.

What is claimed is:

1. A radiation image inspection apparatus comprising:

means for generating and directing radiation toward an article to be inspected;

a screen for converting a radiation pattern of the article into a first visible light image, the screen including a base and a coating disposed on the base and formed of a material exhibiting fluorescence when struck with incident radiation, the coating being selected from a group of materials consisting of scandium, yttrium and the elements of the lanthanide series of rare earth elements having atomic numbers between 57-71, as well as mixtures thereof;

lens means for maintaining the intensity of a first visible light image produced on the screen;

camera means having an image tube target and producing an electrical output system corresponding to the incident image on the image tube target from the lens means; and control means for controlling the operation of a camera means and the radiation generating means, the control means including means for operating the radiation generating means and the camera means in a first mode of operation and a second mode of operation, the first mode being where the radiation generating means is continually energized at a first intensity level and the output from the camera means is blanked for a preset amount of time before the camera means output is energized to generate the electrical signal corresponding to the light image impinging upon the image tube target of the camera means, and the second mode being where both the camera means and the radiation generating means are pulsed, with the radiation generating means being pulsed at an substantially higher second intensity level to generate an output from the camera means during said pulse.

2. The radiation image inspection apparatus of claim 1 wherein the radiation generating means produces x-rays.

3. The radiation inspection apparatus of claim 1 wherein the lens means includes at least one lens.

4. The radiation inspection apparatus of claim 3 wherein the lens means comprises a plurality of co-axially aligned lenses.

5. The radiation inspection apparatus of claim 2 wherein the lens means are formed of leaded glass to block the radiation from passing therethrough.

6. A radiation image inspection apparatus for inspecting articles comprising:

a radiation source for generating and directing x-rays toward the article;

a screen mounted on the opposite side of the article from the radiation generating means for converting the radiation pattern of the article into a first visible light image, the screen having a substrate and a coating disposed on one side of the substrate formed of a material which exhibits fluorescence when struck with incident radiation, the coating being formed of an element selected from the group of elements consisting of scandium, yttrium and elements of the lanthanides rare earth element series having atomic numbers 57-71, and mixtures thereof;

a plurality of lenses co-axially aligned with the screen for maintaining the intensity of the first light image produced on the screen;

camera means having an image tube target for producing an electrical output corresponding to the incident light image incident on the image tube target; and control means for controlling the operation of the camera means and the x-ray generating means, the camera means operating the radiation generating means and the camera means in a first mode of operation in which the radiation generating means is continually energized and the output from the camera means is blanked for a preset amount of time before the camera means output is energized to generate the electrical signal corresponding to the light image impinging upon the image tube screen of the camera means and a second mode of operation in which both the camera means and the radiation generating means are pulsed, with the radiation generating means being pulsed at an substantially higher second intensity level to generate an output from the camera means during the pulse.

7. A method for producing a visible image of a pattern of penetrating radiation emergent from and around an article comprising the steps of:

directing radiation toward the article such that the radiation passes through and around the article;

converting the radiation pattern to a corresponding first visual image by means of a screen coated with a material exhibiting fluorescent properties which becomes illuminated depending upon the amount of incident radiation striking the coating to produce a first visual image;

passing the first visual image through a plurality of co-axial lenses to maintain the intensity of the light level of the first visual image;

employing a camera having an image tube target which is swept by a scan beam to generate an electrical output signal corresponding to the first image incident on the image tube target; and controlling the operation of the camera and the generator of radiation in either of first or second modes in which radiation is continually energized at a first intensity level eliminating the need for separate light intensifying means and the output from the camera is blanked for a preset amount of time before the camera output is energized to generate the electrical signal corresponding to the light image impinging upon the image tube target of the camera and a second mode of operation in which the camera and the generator of radiation are pulsed, with the radiation being pulsed at an substantially higher second intensity level to generate an output from the camera during the pulse.

* * * * *